United States Patent [19]

Hall et al.

[11] 4,144,333

[45] Mar. 13, 1979

[54] MONOCYCLIC BETA-LACTAMS WITH ANTIBACTERIAL ACTIVITY

[75] Inventors: Ralph F. Hall, Cranbury, N.J.; William F. Huffman, Malvern, Pa.

[73] Assignee: SmithKline Corporation, Philadelphia, Pa.

[21] Appl. No.: 742,149

[22] Filed: Nov. 15, 1976

[51] Int. Cl.$^2$ .................. C07D 205/08; C07D 407/06; C07D 409/06; C07D 413/06
[52] U.S. Cl. .................................... 424/244; 546/275; 260/295 L; 260/302 H; 260/307 A; 260/307 C; 260/307 G; 260/308 R; 260/308 D; 260/326 S; 260/326 N; 260/326.37; 260/332.2 H; 260/347.2; 260/347.3; 424/251; 424/263; 424/269; 424/270; 424/272; 424/274; 424/275; 424/285; 544/298; 544/322; 544/335
[58] Field of Search .................. 260/239 A, 256.4 R, 260/256.5 R, 294.9, 294.8 R, 295 L, 302 H, 308 R, 308 D, 307 A, 307 C, 307 G, 326 N, 326 S, 326.37, 332.2 H, 347.2, 347.3, 347.4; 424/244, 251, 263, 269, 270, 272, 275, 285

[56] References Cited

U.S. PATENT DOCUMENTS

| | | | |
|---|---|---|---|
| 3,840,556 | 10/1975 | Kukolja | 260/239 A |
| 3,883,517 | 5/1975 | Heusler et al. | 260/239 A |
| 3,920,696 | 11/1975 | Kukolja | 260/239 A |
| 3,943,123 | 3/1976 | Bose | 260/239 A |
| 4,000,154 | 12/1976 | Gleason et al. | 260/239 A |

FOREIGN PATENT DOCUMENTS 2437385  2/1975  Fed. Rep. of Germany ....... 260/326 B

OTHER PUBLICATIONS

Abdulla et al., J. Med. Chem., vol. 18, pp. 625–627 (1975).
Hashimoto et al., J. Am. Chem. Soc., vol. 98, pp. 3023–3025 (1976).

*Primary Examiner*—Alton D. Rollins
*Attorney, Agent, or Firm*—Stuart R. Suter; Alan D. Lourie; William H. Edgerton

[57] ABSTRACT

A monocyclic β-lactam containing a cis-β-acylamino moiety as in the penicillin and cephalosporin antibacterials is disclosed. These compounds have antibacterial activity against a variety of Gram-positive and Gram-negative organisms. Intermediates useful for the preparation of these antibacterials are also disclosed.

28 Claims, No Drawings

MONOCYCLIC BETA-LACTAMS WITH ANTIBACTERIAL ACTIVITY

BACKGROUND

β-Lactam antibiotics are an important group of compounds in man's struggle against infectious diseases. The most important β-lactams are the penicillins and cephalosporins which contain another ring system, either thiazine or thiazole, as an intricate part of the total molecule. In general, only bicyclic β-lactams have sufficient antibacterial activity to be commercially useful. Many monocyclic β-lactams have been reported in the literature primarily as degradation products of penicillins or cephalosporins or as synthetic precursors for penicillins and cephalosporins. However, significant biological activity has not been reported for these monocyclic β-lactams. U.S. Pat. Nos. 3,943,123; 3,840,556 and 3,920,696, an article in *J. Med. Chem.* 18, 625 (1975) and German Pat. No. 2,437,385 are illustrative of this point. One exception to this general rule is a monocyclic β-lactam prepared by fermentation and recently reported in *J. Amer. Chem. Soc.*, 98, 3023 (1976).

We have now discovered a new monocyclic β-lactam system which is prepared by a totally synthetic method and which possesses good antibacterial activity.

DESCRIPTION OF THE INVENTION

The compounds of this invention are represented by the following structural formula:

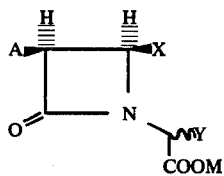

Formula I wherein

A is amino, protected amino or acylamino;

X is $CH_2$-halogen,

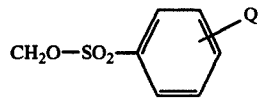

or $CH_2OSO_2R$;

R is lower alkyl;

Q is hydrogen, lower alkyl, or halo;

Y is

or hydroxy;

E is hydrogen, lower alkyl, trifluoromethyl or phenyl, unsubstituted or substituted with one or two substituents selected from the group consisting of lower alkoxy, lower alkyl, halo, and nitro; and M is hydrogen, a carboxylic acid protective ester group, or a pharmaceutically acceptable cation.

The terms lower alkyl, lower alkylthio and lower alkoxy used within this entire disclosure refers to alkyl groups containing one to six carbon atoms. The term halogen or halo includes fluorine, chlorine, bromine and iodine.

Compounds of Formula I where X is chloromethyl, bromomethyl or iodomethyl and E is methyl or phenyl are a preferred group.

Another preferred group of compounds is those compounds which have antibacterial activity. This group of compounds is those of Formula I where A is acylamino, Y is SCOE and M is hydrogen or a pharmaceutically acceptable cation.

Within the term acylamino, acyl refers to any acyl group used within the semisynthetic cephalosporin and penicillin art. Examples of many of these well known groups are set forth in "Cephalosporins and Penicillins", ed. Flynn, Academic Press 1972; U.S. Pat. No. 3,953,424 and 3,953,436. Preferred acyl groups are presented by the general formulae:

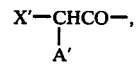

$Y'$—$CH_2$—CO—, or Z—$S(O)_n CH_2 CO$— where

X' is thienyl, furyl, cyclohexyl, cyclohexenyl, cyclohexadienyl, phenyl or phenyl substituted with one or two substituents selected from the group consisting of lower alkyl, lower alkoxy, hydroxy, hydroxymethyl, halo, nitro, amino, aminomethyl, mercapto, lower alkylthio, trifluoromethyl, ureido, formamido, and carboxymethylamino;

A' is amino, hydroxy, formyloxy, carboxyl, sulfo or (when the α-hydrogen is absent) methoxyimino or oximino;

Y' is cyano, azido, phenyl, phenoxy, 2-aminomethylphenyl or a 5 or 6-membered heterocyclic ring containing carbon and 1–4 heteroatoms selected from the group consisting of nitrogen, oxygen and sulfur;

Z is phenyl, pyridyl, lower alkyl, trifluoromethyl, trifluoroethyl, or cyanomethyl; and n is 0, 1 or 2.

The 5- or 6-membered heterocycles include thienyl, furyl, thiazoyl, isothiazolyl, oxadiazolyl, thiadiazolyl, triazolyl, tetrazolyl, sydnone, pyridyl, pyrimidyl and the like. Each heterocyclic group may be unsubstituted or substituted with one or two substituents selected from lower alkyl, halo, hydroxy, nitro, amino, lower alkoxy, aryl such as phenyl, lower aralkyl and the like.

Particularly preferred acyl groups include the following examples:

phenylacetyl
α-hydroxyphenylacetyl
α-formyloxyphenylacetyl
α-aminophenylacetyl
α-amino-4-hydroxyphenylacetyl
α-amino-4-hydroxy-3-fluorophenylacetyl
trifluoromethylmercaptoacetyl
methylmercaptoacetyl
methylsulfonylacetyl
2,2,2-trifluoroethylsulfinylacetyl
cyanoacetyl
cyanomethylmercaptoacetyl
α-carboxy-2-thienylacetyl
α-carboxy-3-thienylacetyl
α-carboxyphenylacetyl
α-sulphophenylacetyl
3-sydnoneacetyl
2-thienylacetyl
1-tetrazolylacetyl phenoxyacetyl
4-pyridylmercaptoacetyl
(2-aminomethylphenyl)acetyl
syn-α-methoxyimino-(2-furyl)acetyl
α-oximinophenylacetyl
2,6-dimethoxybenzoyl The term "a carboxylic acid protective ester group" refers to those ester groups which are commonly employed to block or protect the carboxylic acid functionality while reactions are carried out on other functional groups within the molecule. The term has acquired a definite meaning within the β-lactam and organic chemical arts and many useful groups within this term are known in the art. These protective groups are known for the ease with which they may be cleaved to regenerate the carboxylic acid group. Cleavage can be affected by known methods including hydrolytic and hydrogenation methods.

Known ester protecting groups include lower alkyl such as methyl, 2,2,2-trichloroethyl, β-iodoethyl, $C_4$–$C_6$-tert-alkyl, such as t-butyl, $C_5$–$C_7$-tert-alkenyl, $C_5$–$C_7$-tert-alkynyl, $C_1$–$C_6$-alkanoylmethyl, N-phthalimidomethyl, benzoylmethyl, halobenzoylmethyl, methylbenzoylmethyl, methanesulfonylbenzoylmethyl, phenylbenzoylmethyl, benzyl, p-nitrobenzyl, p-methoxybenzyl, benzhydryl, trityl, trimethylsilyl, triethylsilyl and the like. The choice of which ester group to use is well within the ability of one skilled in the art. Factors which are considered include what subsequent reaction conditions the group must withstand and what conditions for removing the protecting ester is desirable. Groups which are removed by treatment with trifluoroacetic acid, hydrogenation or zinc dust and acetic acid have been preferred in the art when a β-lactam is fused to a six-member ring and are found to be particularly useful in this invention. The choice of the protecting group is not critical to our invention since the novelty of our invention lies within the new monocyclic nucleus and not the ester substituents.

"Protected amino" is a term well known in the art. It refers to amino groups which have been masked by another group so as to protect them during subsequent chemical reactions and then the masking group can be removed to generate again the desired amino moiety. Many groups are known and used for this purpose within the penicillin, cephalosporin, and peptide synthetic arts. Examples of these include, t-butoxycarbonyl, trichloroethoxycarbonyl, benzyloxycarbonyl, p-methoxybenzyloxycarbonyl, p-nitrobenzyloxycarbonyl, isobornyloxycarbonyl, trityl, methyl acetoacetate adduct and the like which are monovalent protecting groups. Divalent protecting groups include phthaloyl, succinyl, maleyl, and the 4,5-diphenyl-4-oxazolin-2-one group. Preparation and removal of the 4-oxazolin-2-one group is taught in the art; *J Org. Chem.*, 38 3034 (1973). The choice of the protecting group depends on various factors including the subsequent chemical reaction conditions and the desired conditions for removal of the protecting group. However, this choice is within the ordinary ability of one skilled in the art. Again the choice of the amino protecting group is not critical to our invention for the same reasons given above regarding the carboxyl protecting group.

The above definition of amino and carboxyl protecting groups is not intended to be exhaustive. A person skilled in the art knows the purpose of these groups and is able to properly choose from the groups known and described in the art. Many articles and books have described the subject of protecting reactive groups, for example J. F. W. McOmie, "Protective Groups in Organic Chemistry", Plenum Press, 1973.

The term "pharmaceutically acceptable cation" is also a well known term in the art. Many bases are known and used to prepare salts of carboxylic acids for pharmaceutical formulations. These salts have improved properties, such as solubility, over the free acids. Examples of useful cations include alkali metals such as sodium and potassium, alkali earth metals and ammonium cations from inorganic or organic amine bases. These salts are prepared by standard methods from the appropriate base and the carboxylic acid.

Also included within the scope of this invention is the salts of other acid or base moieties present in the compounds, for example, within the acyl group or when A is amino. Salts of base moieties are prepared from well-known inorganic and organic acids used in the field such as maleic, fumaric, acetic, propionic, tartaric, citric, hydrochloric, hydrobromic, sulfuric, cyclohexylsulfamic and phosphoric acids and the like. These salts are all prepared by standard methods known and used in the art and readily apparent to one skilled in the art.

The compounds of this invention may exist in hydrate or solvate form. The amount of water or solvent may vary. These various forms of the compounds of this invention are also part of the invention disclosed and claimed herein.

The compounds of this invention where A is acylamino and M is hydrogen or a pharmaceutically acceptable cation have antibacterial activity against Gram-positive and Gram-negative organisms. Minimum inhibitory concentrations (MIC's) against a variety of bacteria is shown in Table 1 for representative compounds. Data for a standard antibacterial agent, cephalothin, is included. Antibacterial activity is also observed when the compounds are tested in a standard in vivo screening test.

The active compounds or their salts can be formulated into pharmaceutical compositions useful for the treatment or prevention of bacterial infections in warm-blooded mammals such as man. For example, the salts of the active compounds can be dissolved in sterile water, sterile normal saline and the like to give a liquid pharmaceutical formulation which can be administered parenterally to the subject. The compounds can also be formulated into forms suitable for oral administration in the same manner as oral penicillins and cephalosporins. Daily dosages depend on various factors including the severity of the infection and the age and weight of the subject. In general, daily dosages range from about 1–5 g which may be divided into smaller unit doses if desired.

TABLE I

| | | | | | | | MINIMUM INHIBITORY CONCENTRATION (μg/ml) | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Compound (See Table II for structure) | Staph. aureus HH127 | Staph. aureus SK&F23390 | Staph. aureus Villaluz (M.R.) SK&F70399 | Strep. faecalis HH34358 | E.coli SK&F12140 | E.coli HH33779 | Kleb. pneumoniae SK&F4200 | Kleb. pneumoniae SK&F1200 | Salmonella paratyphi ATCC12176 | P.mirabilis PM-444 | Pseudo aerugi- nosa HH63 | Serratia marcescens ATCC13880 | Proteus morgani 179 | Enterobacter aerogenes ATCC13048 | Enterobacter cloacae HH31254 |
| 1 | >200 | 3.1 | >200 | 100 | 50 | 50 | 12.5 | 25 | 12.5 | — | >200 | >200 | >200 | 50 | 50 |
| 2 | >200 | 12.5 | >200 | 50 | 25 | 25 | 3.1 | 12.5 | 3.1 | 6.3 | >200 | 100 | >200 | 50 | 25 |
| 3 | 25 | 25 | >200 | 200 | 200 | 100 | 50 | 100 | 50 | 25 | >200 | >200 | 200 | 100 | 100 |
| 4 | >200 | 3.1 | >200 | 50 | 6.3 | 12.5 | 1.6 | 3.1 | 0.8 | 3.1 | 200 | 50 | 50 | 12.5 | 6.3 |
| 5 | >200 | 3.1 | >200 | 100 | 3.1 | 6.3 | 1.6 | 3.1 | 1.6 | 1.6 | >200 | >200 | 100 | 12.5 | 6.3 |
| 6 | >200 | 12.5 | >200 | 100 | 25 | 50 | 12.5 | 25 | 6.3 | 12.5 | 200 | 200 | 200 | 100 | 50 |
| 7 | >200 | 50 | >200 | >200 | 100 | 100 | 50 | 50 | 100 | 50 | >200 | >200 | >200 | 200 | 100 |
| 8 | >200 | 50 | >200 | 200 | 25 | 50 | 6.3 | 12.5 | 3.1 | 6.3 | >200 | 50 | 50 | 25 | 50 |
| 9 | >200 | 100 | >200 | 100 | 6.3 | 12.5 | 6.3 | 12.5 | 1.6 | 6.3 | >200 | 50 | >200 | 6.3 | 6.3 |
| 10 | >200 | 100 | >200 | 100 | 100 | 100 | 50 | 50 | 50 | 50 | 200 | 50 | >200 | 50 | 50 |
| 11 | >200 | 100 | >200 | 100 | 100 | 100 | 100 | 100 | 50 | 100 | 200 | 100 | >200 | 100 | 100 |
| 12 | >200 | 100 | >200 | >200 | 6.3 | 6.3 | 1.6 | 6.3 | 1.6 | 6.3 | 200 | 6.3 | 6.3 | 6.3 | 3.1 |
| cephalothin | 0.2 | 0.2 | 50 | 12.5 | 6.3 | 6.3 | 1.6 | 1.6 | 0.8 | 3.1 | >200 | >200 | >200 | 12.5 | 6.3 |

TABLE II

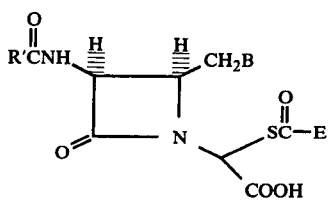

| Compound | R' | B | E |
|---|---|---|---|
| 1 | $C_6H_5OCH_2$ | I | $CH_3$ |
| 2 | $C_6H_5CH_2$ | Br | $CH_3$ |
| 3 | $2,6\text{-}(CH_3O)_2C_6H_3$ | Br | $CH_3$ |
| 4 | Thienyl-$CH_2$ | I | $CH_3$ |
| 5 | Thienyl-$CH_2$ | Br | $CH_3$ |
| 6 | Thienyl-$CH_2$ | Cl | $CH_3$ |
| 7 | Thienyl-$CH_2$ | OTs | $CH_3$ |
| 8 | Thienyl-$CH_2$ | I | $C_6H_5$ |
| 9 | $C_6H_5CH(OH)$ | I | $CH_3$ |
| 10 | $C_6H_5CH(NH_2)$ | I | $CH_3$ |
| 11 | $C_6H_5CH(NH_2)$ | Br | $CH_3$ |
| 12 | $C_6H_5CH(COOH)$ | Br | $CH_3$ |

The compounds of this invention where A is amino or protected amino and/or M is a carboxylic acid protecting ester group are useful as intermediates for the preparation of the active compounds. When A is protected amino, removal of the protecting group gives the free amino group which can be acylated to give, after removal of any protecting groups, the antibacterial agents.

The compounds within this invention where Y is hydroxy are also useful as intermediates for the preparation of the antibacterial agents disclosed herein.

The compounds of this invention are novel monocyclic β-lactams which are prepared by a totally synthetic route. The key starting material is methyl cis-1-(2,4-dimethoxybenzyl)-3-azido-4-oxoazetidine-2-carboxylate (1). This compound is prepared in good yield

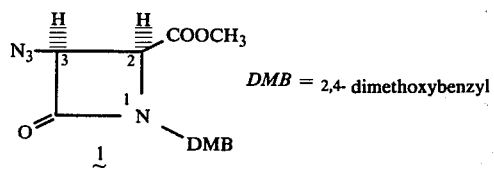

DMB = 2,4- dimethoxybenzyl via a ketene-imine cyclization reaction.

It is readily apparent that conversion of compound 1 into the compounds of Formulae I involves modification of the substituents at positions 1, 2 and 3. Three different approaches for performing these modifications are outlined in Schemes I, II and III. However, a person skilled in the art will also appreciate that these modifications can be carried out via a variety of methods and in various sequences.

The reaction sequence set forth in Scheme I involves first the reduction of the azido moiety of compound 1 to an amino group. The reduction can be affected by catalytic or chemical methods such as zinc and acetic acid. The amino group is blocked with a protecting group. Preferred protecting groups in this sequence of reactions are those which are removed by treatment with trifluoroacetic acid. Examples of such groups include the isobornyloxycarbonyl and the t-butoxycarbonyl groups. The use of the isobornyloxycarbonyl as an amino protecting group is described in *Chem. Pharm. Bull.*, 20, 1017 (1972). The protected amino derivative 2 is treated with a hydroxyl radical producing agent, such as potassium persulfate, which cleaves the dimethoxybenzyl group to give derivative 3. Reduction of the ester group with sodium borohydride gives the alcohol which is treated with a substituted benzenesulfonyl chloride, for example tosyl chloride, or with an alkanesulfonyl choride, for example mesyl chloride to give the sulfonate derivative 4.

Compound 4 is treated with a halide salt such as LiBr, NaI, or LiCl to give the halo derivative. Addition of an ester of glyoxylic acid gives alcohol compound 5. Benzyl, methyl or ethyl esters which hydrolylyze with weak base or benzhydryl (diphenylmethyl) which is cleaved by trifluoroacetic acid are particularly useful. The addition reaction can be affected by acid catalysis with boron trifluoride and the like or an anionic addition method which involves generating the β-lactam nitrogen anion by treatment with a strong base such as butyllithium. Treatment of 5 with thionyl chloride and then with the salt of a thiolcarboxylic acid such as potassium thiolacetate gives 6. Removal of the amino protecting group by treatment with trifluoroacetic acid gives compound 7 where R is an ester protecting group or hydrogen when the ester protecting group is one which is removable with trifluoroacetic acid such as benzhydryl.

SCHEME I

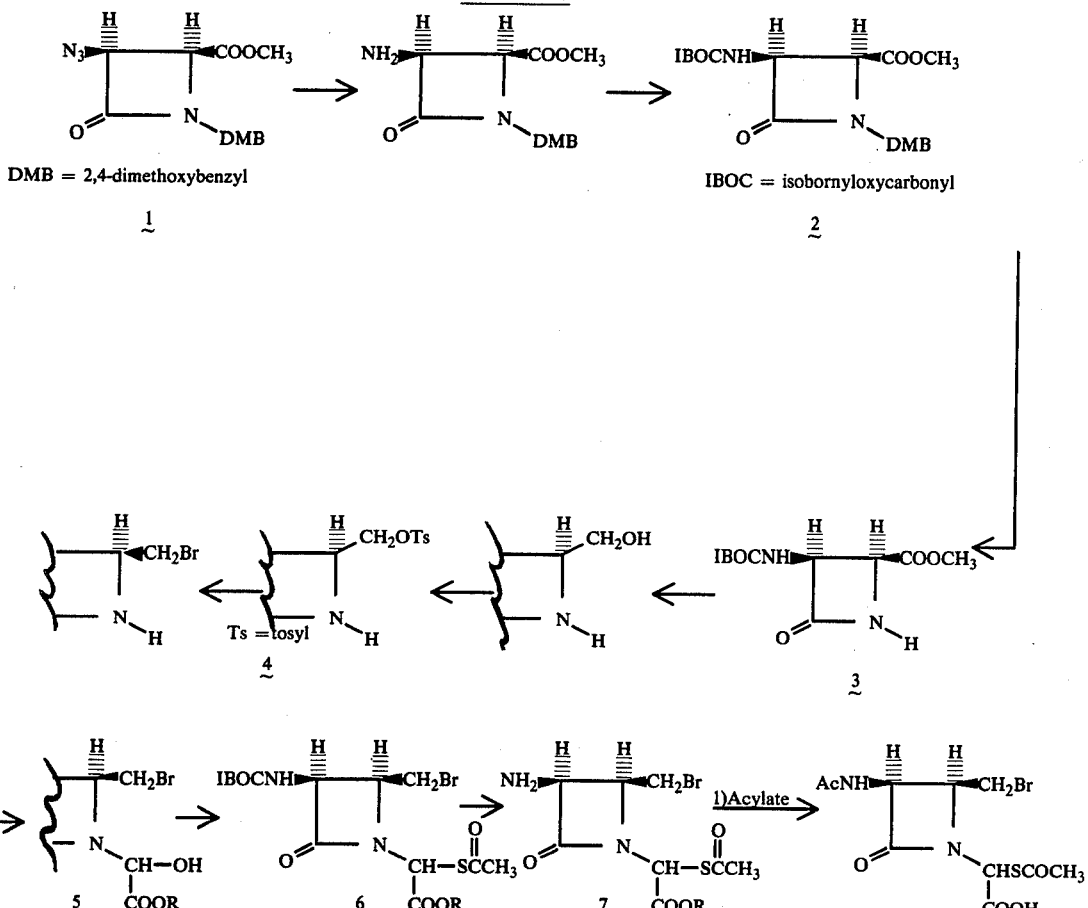

DMB = 2,4-dimethoxybenzyl

IBOC = isobornyloxycarbonyl

Ts = tosyl

Acylation of 7 by standard methods followed by removal of any protecting groups gives the antibacterial compounds of this invention.

The active compounds where X of Formula I is the methylene alkyl or arylsulfonate substituents can be prepared as outlined in Scheme I by elimination of the halide salt displacement reaction; that is, the sulfonate derivative 4 is reacted with a glyoxylate ester and the product is carried forward as described above.

An alternative sequence of reactions to prepare the active compounds is illustrated in Scheme II. The azido-β-lactam 1 is converted to compound 8 by removal of the dimethoxybenzyl group, reduction of the ester to the alcohol and conversion of the alcohol to the sulfonate derivative such as the p-toluenesulfonate. These three reactions use the same general procedures which are set forth above in the discussion of Scheme I. The azido group of compound 8 is reduced by chemical or catalytic hydrogenation to give the amino-β-lactam which is acylated with the desired acyl moiety to give 9. Displacement of the sulfonate substituent with halide ion followed by condensation with an ester of glyoxylic acid, both by procedures given above, yields derivative 10. Conversion of the hydroxy group in 10 to chloro is effected by treatment with thionyl chloride or similar reagent. The chloro derivative is reacted with a salt of a thiolcarboxylic acid such as potassium thiolacetate to give, after removal of any protecting groups by standard methods, the active compounds such as 11. Again, if a 2-methylsulfonate derivative is desired the halide displacement reaction is omitted from the sequence.

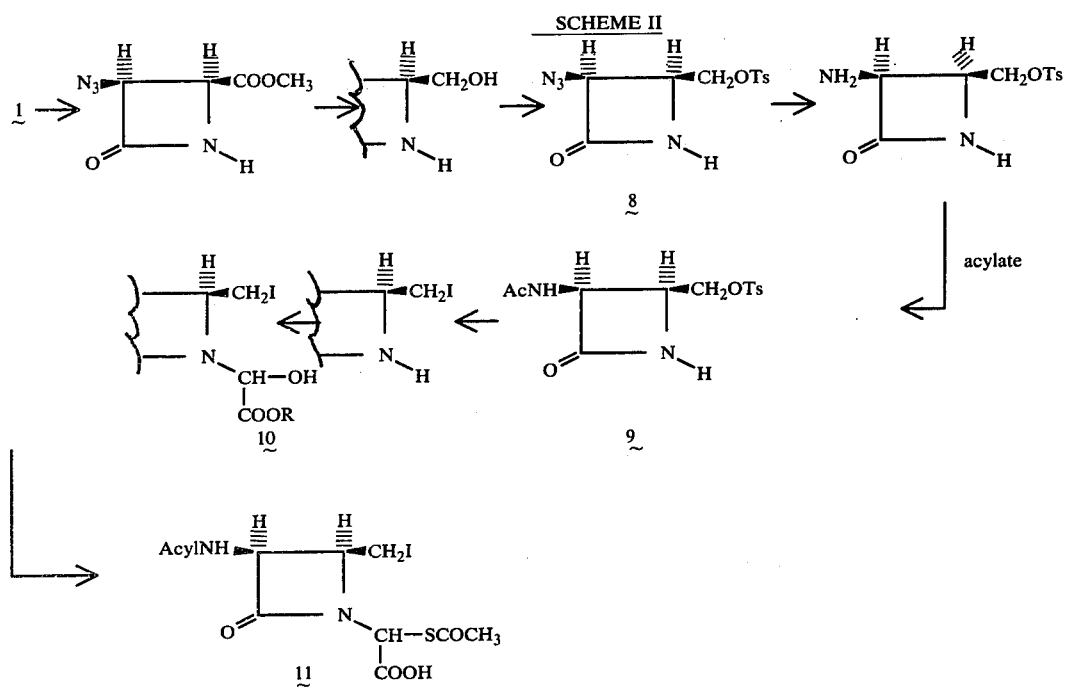

Scheme III presents another sequence of reactions which differs from those presented in Schemes I and II in that the azido group is not reduced to an amino group until the desired modifications at positions 1 and 2 have been completed. Therefore, compound 8 is converted into compound 12 by reactions previously outlined in regard to Schemes I and II. The azido group is reduced to an amino derivative which is acylated with the desired acyl group. Any protecting groups are removed by standard methods to give the novel antibiotic agents.

Acylation of the 3-amino-2-azetidinone compounds of this invention is effected by standard methods. The carboxylic acid group which will be the carbonyl group of the acyl moiety is activated by known methods including mixed anhydride, activated esters, and acid halides. In addition, use of coupling reagents such as dicyclohexylcarbodiimide and carbonyldiimidazole is a possible method of acylation. During the acylation any sensitive group in the acyl moiety, for example hydroxy, amino or carboxyl, can be protected by a standard protecting group such as those described previously. At the appropriate time, which was suggested in the above discussion of preparation of these compounds or at such other time which would be readily apparent to one skilled in the art, the protecting group can be removed.

The sidechain moiety attached to the nitrogen of the β-lactam ring contains an asymmetric carbon thereby giving rise to optical isomers. In addition, the β-lactam ring system is formed as a mixture of d and l optical isomers. Separation of isomers is possible by standard methods of fractional crystallization. It is to be understood that each separate diastereomer as well as diastereomeric mixtures are within the scope of this application.

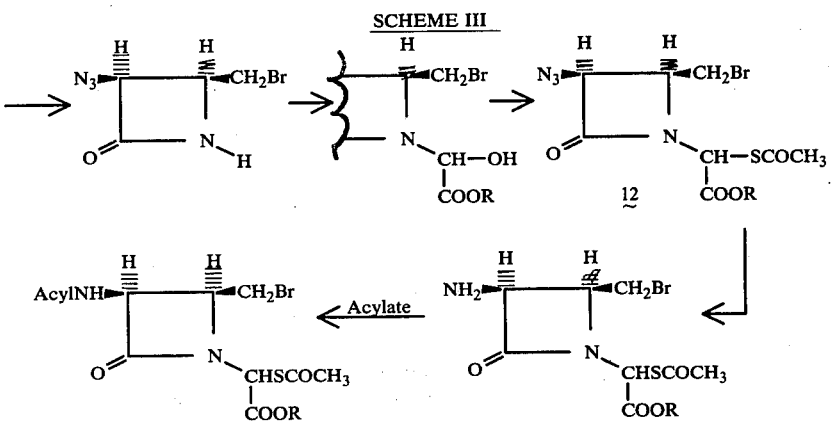

Various acyl sidechains which are particularly useful also contain an asymmetric carbon atom. It is understood that each optical isomer separately and as well as mixtures of the isomers are within the scope of this invention. It has been found that the D-isomer is particularly useful and therefore is a preferred isomer as with the phenylglycyl or mandelyamino containing compounds.

The starting materials necessary to prepare the compounds are commercially available, prepared by known methods or described herein.

The following examples are presented to illustrate general methods of preparing the compounds of this invention to one skilled in the art and are not to be construed as limitative of the scope thereof. All temperatures are given in degrees Centigrade.

PREPARATION 1

Methyl N-(2,4-dimethoxybenzyl)iminoacetate

To a mixture containing 16.82 g (0.101 mol) of 2,4-dimethoxybenzylamine and anhydrous magnesium sulfate in 150 ml of methylene chloride at 25° is added a solution of 10.05 g (0.114 mol) of methyl glyoxylate in 20 ml of methylene chloride. The reaction mixture is stirred at room temperature overnight (15 hours) and then is filtered and the solvents are removed in vacuo to afford the imine as a dark orange gum.

PREPARATION 2

Isobornyl chloroformate

Into an argon flushed flask is placed 82 ml (100 mmol) of a 12.5% phosgene in benzene solution and 100 ml of ether. The solution is cooled to 0° under argon and treated dropwise over a one-hour period with a solution of 11.7 g (76 mmol) dl-isoborneol and 6.7 ml (83.7 mmol) pyridine in 50 ml ether. The solution is allowed to warm to room temperature, stirred 2.5 hours, and then filtered. The solid is washed with ether and the filtrate is evaporated in vacuo to give 15.25 g of product.

PREPARATION 3

Methyl cis-3-azido-1-(2,4-dimethoxybenzyl)-4-oxoazetidine-2-carboxylate (1)

Method A:

To a solution of 15.1 g (0.149 mol) of azidoacetic acid in 130 ml of anhydrous methylene chloride at 0° (ice bath) is added dropwise 21.0 ml (0.15 mol) of trifluoroacetic anhydride. This mixture is stirred at 0° for 15 minutes and then 20.8 ml (0.15 mol) of triethylamine is added dropwise. Stirring is continued for an additional 45 minutes and then the entire reaction mixture is transferred under argon into an additional funnel which is cooled externally by dry ice. The addition funnel is attached to a flask containing the imine from Preparation 1, anhydrous methylene chloride (200 ml), and triethylamine (20.8 ml, 0.15 mole). The solution of the mixed anhydride is added dropwise from the additional funnel to the solution of imine at 0°. Stirring is continued at 0° for 1 hour and then the dark reaction mixture is transferred to a separatory funnel and washed with water, aqueous NaHCO$_3$ and brine and then dried over anhydrous magnesium sulfate. The solvents are removed in vacuo and the residue is chromatographed on 300 g of silica gel (70–230 mesh) affording an off-white solid which is further purified by trituration with ether to give 14.45 g (45%) of the title product as a white solid; tlc: benzene: ethyl acetate (1:1), silica gel GF, Rf = 0.64. Recrystallization from ethyl acetate-hexane affords an analytical sample, mp 82°–84°.

Method B:

A solution of 1.6 g (9.55 mmol) dimethoxybenzylamine in 5 ml of methylene chloride is rapidly added at 0° to a solution of 1.06 g (10 mmol) freshly distilled methyl glyoxylate in 15 ml CH$_2$Cl$_2$. A slight exotherm occurred and water droplets appeared. Magnesium sulfate (5 g) is added and the mixture stirred at 0° for 2 hours. Fresh magnesium sulfate (1.0 g) is added, the magnesium sulfate removed by filtration under argon and washed with a minimum of methylene chloride.

To a solution of 3.8 g (36 mmol) of azidoacetic acid (pumped in high vacuum 3 hr) in 125 ml of methylene chloride is added 10.6 ml (76 mmol) of triethylamine with cooling. Magnesium sulfate (3 g) is added, the mixture stirred 10 minutes at room temperature, filtered under argon and washed with 25 ml methylene chloride.

The azidoacetic acid solution is added at 0° to the imine, sufficient methylene chloride is added to bring the total volume to 200 ml, the solution is cooled to 0° under argon and 5.3 ml (38 mmol) trifluoroacetic anhydride added slowly over 30 minutes with vigorous stirring and cooling. The mixture is stirred for 1 hr at 0°, allowed to warm to room temperature; transferred to a separatory funnel; washed with water, 5% NaHCO$_3$, 2% phosphoric acid and 5% NaHCO$_3$; dried over magnesium sulfate-charcoal; filtered and the filtrate is retreated twice with charcoal and evaporated to dryness. The residue is dissolved in a minimum of ether and stored at −20° to allow crystallization. The crystalline mass is isolated and washed with cold ether to give 1.9 g (64%) product, mp 79°–80.5°.

Method C:

A solution of 1.6 g of 2,4-dimethoxybenzylamine in 15 ml of methylene chloride is shaken with an excess of magneisum sulfate then reacted with 1.05 g of methyl glyoxylate in 2 ml of methylene chloride at 25° (room temperature) overnight. The mixture is filtered, stripped and degassed with argon.

A solution of 1.5 g of azidoacetic acid in 25 ml of methylene chloride is cooled to 0° then reacted with 1.3 ml of oxalyl chloride with 1.2 ml of pyridine in 3 ml of methylene chloride at 0°. Argon is passed through the mixture which is stirred for one hour.

The imine from above is taken into 20 ml of methylene chloride with 4.15 ml of triethylamine. The solution of azidoacetyl chloride is added dropwise at 0°. After one hour at 0° the mixture is washed with water, sodium bicarbonate solution, and brine, dried and stripped. After passing over a silica gel column with methylene chloride the yield is 1.31 g of the desired compound.

PREPARATION 4 cis-3-Azido-4-oxo-2-azetidinylmethyl tosylate

Methyl cis-3-azido-1-(2,4-dimethoxybenzyl)-4-oxoacetidine-2-carboxylate is reacted with potassium persulfate and sodium monohydrogen phosphate according to the procedure of Example 4 to give methyl cis-3-azido-4-axoazetidine-2-carboxylate. The methyl ester of this product is reduced by treatment with sodium borohydride according to the procedure of Example 5 to give the methyl alcohol derivative. The alcohol is converted into the title compound by treatment with p-toluenesulfonyl chloride according to the procedure of Example 6; mp 77°–78°.

EXAMPLE 1

Methyl cis-1-(2,4-Dimethoxybenzyl)-3-amino-4-oxoazetidine-2-carboxylate

A mixture containing 10.0 g (0.312 mol) of methyl cis-1-(2,4-dimethoxybenzyl)-3-azido-4-oxoazetidine-2-carboxylate, 1.0 g of 10% palladium on carbon, and 200 ml of ethanol is hydrogenated for 2 hrs at 40°–45° at 60 psi of hydrogen. The reaction mixture is allowed to cool to 25° and is filtered through filter-aid. After removing the solvents in vacuo a clear, yellow gum of the title product is obtained.

EXAMPLE 2

Methyl cis-3-t-Butoxycarbonylamino-2-(2,4-dimethoxybenzyl)-4-oxoazetidine-2-carboxylate A solution of 5.5 g (18.8 mmol) of methyl cis-3-amino-1-(2,4-dimethoxybenzyl)-4-oxoazetidine-2-carboxylate in 100 ml of dry toluene is cooled to −78°; 2.5 ml (18.8 mmol) of triethylamine is added followed by rapid addition of 35 ml (42 mmol) of a 12% solution of phosgene in benzene. The mixture is stirred 15 min at −78°, 3 hr at −45° (acetonitrile-dry ice), then warmed to room temperature and concentrated to half volume in vacuo. To the resulting solution is added 50 ml of t-butanol and the mixture is stirred at room temperature overnight. The solvents are removed in vacuo, the residue is diluted with ethyl acetate and filtered. The filtrate is transferred to a separatory funnel and washed with 5% $NaHCO_3$, 5% HCl and brine; dried over magnesium sulfate and evaporated to dryness. Recrystallization of the crude, crystalline product affords 3.8 g (52%) of the title compound. Recrystallization from ether gives an analytical sample.

EXAMPLE 3

Methyl cis-3-isobornyloxycarbonylamino-1-(2,4-dimethoxybenzyl)-4-oxoazetidine-2-carboxylate (2)

A solution of 11.5 g (53.7 mmol) of isobornyl chloroformate in 75 ml methylene chloride, is cooled to −78° in an argon flushed flask. To this solution is added dropwise a mixture of 7.75 g (26.3 mmol) of the 3-amino product from Example 1 and 3.4 g (26.3 mmol) of diisopropylethyl amine in 150 ml methylene over a 1.5 hour period with cooling to −78°. The reaction is stirred at −78° for 1–3 hours and then allowed to stand overnight at −25°. To the solution is added 10 ml of cold 1N $H_2SO_4$ and the organic solvent is removed. The residue is dissolved in ethyl acetate which is then washed with two portions of cold 1N $H_2SO_4$, two portions aqueous $NaHCO_3$ and saturated NaCl. The dried solution is evaporated and the residue is chromatographed on silica gel with a gradient of 0% to 15% ethyl acetate in methylene chloride as eluant to give 9.7 g of product.

EXAMPLE 4

Methyl cis-3-Isobornyloxycarbonylamino-4-oxoazetidine-2-carboxylate (3)

A degassed solution of 4.75 g (10 mmol) of the product from Example 3 in 128 ml acetonitrile is heated to reflux. To the refluxing solution is added in six portions over a period of one hour a degassed solution of 10.81 g (40 mmol) $K_2S_2O_8$ and 5.36 g (20 mmol) $Na_2HPO_4 \cdot 7H_2O$ in 200 ml water. When tlc analysis indicates the reaction is complete, the solution is cooled, the organic solvents are evaporated in vacuo and, after the addition of water, the aqueous phase is extracted with ethyl acetate. The dried extracts are concentrated and the residue is chromatographed on silica gel with a gradient of 0% to 50% et acetate in benzene as eluant to give 2.57 g (79%) of the title compound.

EXAMPLE 5 cis-3-Isobornyloxycarbonylamino-4-oxo-2-azetidinylmethyl alcohol

A solution of 2.5 g (7.7 mmol) of the product from Example 4 in 154 ml tetrahydrofuran and 17 ml water under argon is cooled to 0° and treated with a solution of 582 mg (15.4 mmol) of $NaBH_4$ in 40 ml cold water. The reaction is stirred for 1–2 hours at 0° and then at −25° overnight. Excess reagent is destroyed by the addition of 2 ml glacial acetic acid. The organic solvent is removed, additional water is added and the aqueous solution is extracted with ethyl acetate. The extracts are washed with saline solution, dried and evaporated to a residue which is recrystallized from ethyl acetate/ether/hexane; 1.42 g (63%) mp 152.5°–154°.

EXAMPLE 6 cis-3-Isobornyloxycarbonylamino-4-oxo-2-azetidinylmethyl tosylate (4)

A solution of 1.185 g (4 mmol) of the alcohol product of Example 5 in 7.0 ml pyridine under argon is cooled to 0° and then 1.525 g (8 mmol) p-toluenesulfonyl chloride in 2.4 ml pyridine is added. The reaction is stirred at 0° until tlc analysis indicates that the reaction is completed. To the mixture is added 0.38 ml 85% lactic acid. After stirring 1 hour at 0°, the reaction is poured into ethyl acetate and the resulting solution is washed twice with water, each of the following: 1N $H_2SO_4$, saturated $NaHCO_3$ and saturated NaCl. The dried solution is evaporated to give the title product; 2.0 g (100%).

EXAMPLE 7 cis-3-Isobornyloxycarbonylamino-4-oxo-2-azetidinylmethyl bromide

To a mixture of 326 mg (3.75 mmol) LiBr in 4.5 ml dry dimethylformamide is added 338 mg (0.75 mmol) of the tosylate of Example 6. The mixture is degassed with argon and heated to 60° for 4 hours. The reaction is poured into ethyl acetate and washed well with water and saturated NaCl. The dried solution is evaporated to give 75% yield of the title compound.

EXAMPLE 8

Benzhydryl α-(cis-3-Isobornyloxycarbonylamino-2-bromomethyl-4-oxo-1-azetidinyl)-α-hydroxyacetate (5)

The bromo compound of Example 7 (800 mg, 2.23 mmol) is dissolved in 20 ml tetrahydrofuran, cooled to −78° under argon, and treated with 1.22 ml (2.4 mmol) of 1.97M butyllithium in hexane. After stirring for 30 minutes at −78°, a solution of 577 mg (2.4 mmol) benzhydryl glyoxylate in 5 ml tetrahydrofuran is added. The reaction is stirred 2 hours at −78°, quenched with a cold $NaH_2PO_4$ solution, and extracted with ethyl acetate. The extracts are washed with saline, dried and evaporated to give the title product.

EXAMPLE 9

Benzhydryl (cis-3-Isobornyloxycarbonylamino-2-bromomethyl-4-oxo-1-azetidinyl)thioacetoxyacetate (6)

To a cold (−10° with CCl$_4$/dry ice) solution of 943 mg (1.57 mmol) of product from Example 8 in 20 ml dry tetrahydrofuran under argon is added 161 μl (2.0 mmol) pyridine and then 144 μl (2.0 mmol) of thionyl chloride. The solution is stirred at −10° for 15 minutes and then a solution of 228 mg (2.0 mmol) potassium thiolacetate in 20 ml dimethylformamide is added. After stirring 2 hours at −10°, the tetrahydrofuran is removed in vacuo and the residue is poured into ethyl acetate. The solution is washed with water and sodium chloride, dried, and evaporated. The residue is chromatographed on 25 g silica gel with an eluant gradient of 0–25% ethyl acetate in methylene chloride to give the product, 44% yield.

EXAMPLE 10

(cis-3-Amino-2-bromomethyl-4-oxo-1-azetidinyl)thioacetoxyacetic acid (7)

The product from Example 9 (195 mg, 0.3 mmol) and 160 μl (1.48 mmol) anisole are combined, cooled to 0°, and then treated with 6 ml trifluoroacetic acid. The reaction is stirred and cooled 1 hour and the trifluoroacetic acid is removed in vacuo. Ether is added to the residue and the precipitated trifluoroacetate salt of the title compound is collected and dried under vacuum.

EXAMPLE 11

When the t-butoxycarbonylamino derivative of Example 2 is substituted for the isobornyloxycarbonylamino derivatives in Examples 4–9, the corresponding t-butoxycarbonylamino derivatives are obtained. Treating benzhydryl (cis-3-t-butoxycarbonylamino-2-bromomethyl-4-oxo-1-azetidinyl)thioacetoxyacetate with trifluoroacetic acid and anisole according to the procedure of Example 10 also gives the trifluoroacetate salt of (cis-3-amino-2-bromomethyl-4-oxo-1-azetidinyl)thioacetoxyacetic acid.

EXAMPLE 12

[cis-3-(2'-Thienylacetamido)-2-bromomethyl-4-oxo-1-azetidinyl]thioacetoxyacetic acid Methylene chloride (5 ml) is added to 63 mg (0.154 mmol) of the salt of the 3-amino compound of Example 10 and the solution is cooled to 0° under argon. To the solution is added 71 μl (0.51 mmol) triethylamine followed by 23 μl (0.18 mmol) 2-thienylacetyl chloride. The reaction is stirred 3 hours at 0°, the methylene chloride is removed in vacuo and the residue is dissolved in ethyl acetate and saturated NaHCO$_3$. The aqueous phase is separated, washed well with ethyl acetate and acidified to pH 2 with dilute HCl. The acidic solution is extracted with ethyl acetate. The dried extracts are evaporated to give the title compound.

EXAMPLE 13

[cis-3-(2,6-Dimethoxybenzamido)-2-bromomethyl-4-oxo-1-azetidinyl]thioacetoxyacetic acid Substitution of 2,6-dimethoxybenzoyl chloride for 2-thienylacetyl chloride in the procedure of Example 12 gives the title product, 62% after preparative tlc on silica gel plates.

EXAMPLE 14

A solution of 3.5 g (7.74 mmol) of the tosylate from Example 6 in 10 ml dimethylformamide (DMF) is added to a solution 3.32 g (78.5 mmol) LiCl in 30 ml DMF. The resulting solution is degassed for 15 minutes with argon and then heated for 3 hours at 73° under argon. After cooling to room temperature, the mixture is taken up in saline solution and extracted with ethyl acetate. The extracts are washed with saline solution, dried and evaporated to give cis-3-isobornyloxycarbonylamino-4-oxo-2-azetidinylmethyl chloride.

Similarly when the tosylate derivative is heated with a 10 mole excess of sodium iodide in acetone at 55°–60° for 6–7 hours, cis-3-isobornyloxycarbonylamino-4-oxo-2-azetidinylmethyl iodide is obtained.

When the above chloro and iodo derivatives are carried through the reaction sequence of Examples 8, 9 and 10, the trifluoroacetate salts of (cis-3-amino-2-chloromethyl-4-oxo-1-azetidinyl)thioacetoxyacetic acid and (cis-3-amino-2-iodomethyl-4-oxo-1-azetidinyl)thioacetoxyacetic acid are obtained.

EXAMPLE 15

When the amino compound prepared in Example 10 is acylated by standard methods known in the art with the appropriate carboxylic acid or activated derivative thereof (all of which are known in the cephalosporin or penicillin arts) in which any sensitive group is appropriately protected, the following products are obtained after removal by standard methods of any protecting group:

[cis-3-phenylacetamido-2-bromomethyl-4-oxo-1-azetidinyl]thioacetoxyacetic acid

[cis-3-(α-hydroxyphenylacetamido)-2-bromomethyl-4-oxo-1-azetidinyl]thioacetoxyacetic acid

[cis-3-(α-aminophenylacetamido)-2-bromomethyl-4-oxo-1-azetidinyl]thioacetoxyacetic acid

[cis-3-(α-amino-4-hydroxyphenylacetamido)-2-bromomethyl-4-oxo-1-azetidinyl]thioacetoxyacetic acid

[cis-3-(α-amino-4-hydroxy-3-fluorophenylacetamido)-2-bromomethyl-4-oxo-1-azetidinyl]thioacetoxyacetic acid

[cis-3-trifluoromethylmercaptoacetamido-2-bromomethyl-4-oxo-1-azetidinyl]thioacetoxyacetic acid

[cis-3-methylmercaptoacetamido-2-bromomethyl-4-oxo-1-azetidinyl]thioacetoxyacetic acid

[cis-3-methylsulfonylacetamido-2-bromomethyl-4-oxo-1-azetidinyl]thioacetoxyacetic acid

[cis-3-(2',2',2'-trifluoroethylsulfinylacetamido)-2-bromomethyl-4-oxo-1-azetidinyl]thioacetoxyacetic acid

[cis-3-cyanoacetamido-2-bromomethyl-4-oxo-1-azetidinyl]thioacetoxyacetic acid

[cis-3-cyanomethylmercaptoacetamido-2-bromomethyl-4-oxo-1-azetidinyl]thioacetoxyacetic acid

[cis-3-(α-carboxy-3'-thienylacetamido)-2-bromomethyl-4-oxo-1-azetidinyl]thioacetoxyacetic acid

[cis-3-(α-carboxyphenylacetamido)-2-bromomethyl-4-oxo-1-azetidinyl]thioacetoxyacetic acid

[cis-3-(3'-sydnoneacetamido)-2-bromomethyl-4-oxo-1-azetidinyl]thioacetoxyacetic acid

[cis-3-(1'-tetrazolylacetamido)-2-bromomethyl-4-oxo-1-azetidinyl]thioacetoxyacetic acid

[cis-3-(4'-pyridylmercaptoacetamido)-2-bromomethyl-4-oxo-1-azetidinyl]thioacetoxyacetic acid

[cis-3-(syn-α-methoxyimino-2′-furylacetamido)-2-bromomethyl-4-oxo-1-azetidinyl]thioacetoxyacetic acid

[cis-3-(2′-aminomethylphenylacetamido)-2-bromomethyl-4-oxo-1-azetidinyl]thioacetoxyacetic acid

[cis-3-(α-oximinophenylacetamido)-2-bromomethyl-4-oxo-1-azetidinyl]thioacetoxyacetic acid

EXAMPLE 16

When (cis-3-amino-2-chloromethyl-4-oxo-1-azetidinyl)thioacetoxyacetic acid is acylated by standard acylation methods known in the art (many of which are illustrated herein) with the appropriate carboxylic acid or an activated derivative thereof in which any sensitive group(s) are appropriately protected, the following products are obtained after removal by standard methods of any protecting group(s):

[cis-3-phenylacetamido-2-chloromethyl-4-oxo-1-azetidinyl]thioacetoxyacetic acid

[cis-3-(α-hydroxyphenylacetamido)-2-chloromethyl-4-oxo-1-azetidinyl]thioacetoxyacetic acid

[cis-3-(α-aminophenylacetamido)-2-chloromethyl-4-oxo-1-azetidinyl]thioacetoxyacetic acid

[cis-3-(α-amino-4-hydroxyphenylacetamido)-2-chloromethyl-4-oxo-1-azetidinyl]thioacetoxyacetic acid

[cis-3-(α-amino-4-hydroxy-3-fluorophenylacetamido)-2-chloromethyl-4-oxo-1-azetidinyl]thioacetoxyacetic acid

[cis-3-trifluoromethylmercaptoacetamido-2-chloromethyl-4-oxo-1-azetidinyl]thioacetoxyacetic acid

[cis-3-methylmercaptoacetamido-2-chloromethyl-4-oxo-1-azetidinyl]thioacetoxyacetic acid

[cis-3-methylsulfonylacetamido-2-chloromethyl-4-oxo-1-azetidinyl]thioacetoxyacetic acid

[cis-3-(2′,2′,2′-trifluoroethylsulfinylacetamido)-2-chloromethyl-4-oxo-1-axetidinyl]thioacetoxyacetic acid

[cis-3-cyanoacetamido-2-chloromethyl-4-oxo-1-azetidinyl]thioacetoxyacetic acid

[cis-3-cyanomethylmercaptoacetamido-2-chloromethyl-4-oxo-1-axetidinyl]thioacetoxyacetic acid

[cis-3-(α-carboxy-3′-thienylacetamido)-2-chloromethyl-4-oxo-1-azetidinyl]thioacetoxyacetic acid

[cis-3-(α-carboxyphenylacetamido)-2-chloromethyl-4-oxo-1-azetidinyl]thioacetoxyacetic acid

[cis-3-(3′-sydnoneacetamido)-2-chloromethyl-4-oxo-1-azetidinyl]thioacetoxyacetic acid

[cis-3-(1′-tetrazolylacetamido)-2-chloromethyl-4-oxo-1-azetidinyl]thioacetoxyacetic acid

[cis-3-(4′-pyridylmercaptoacetamido)-2-chloromethyl-4-oxo-1-azetidinyl]thioacetoxyacetic acid

[cis-3-(syn-α-methoxyimino-2′-furylacetamido)-2-chloromethyl-4-oxo-1-azetidinyl]thioacetoxyacetic acid

[cis-3-(2′-aminomethylphenylacetamido)-2-chloromethyl-4-oxo-1-azetidinyl]thioacetoxyacetic acid

[cis-3-(α-oximinophenylacetamido)-2-chloromethyl-4-oxo-1-azetidinyl]thioacetoxyacetic acid.

EXAMPLE 17

When (cis-3-amino-2-iodomethyl-4-oxo-1-azetidinyl)-thioacetoxyacetic acid is acylated by standard acylation methods known in the art (many of which are illustrated herein) with the appropriate carboxylic acid or an activated derivative thereof in which any sensitive group(s) are appropriately protected, the following products are obtained after removal by standard methods of any protecting group(s):

[cis-3-phenylacetamido-2-iodomethyl-4-oxo-1-azetidinyl]thioacetoxyacetic acid

[cis-3-(α-hydroxyphenylacetamido)-2-iodomethyl-4-oxo-1-azetidinyl]thioacetoxyacetic acid

[cis-3-(α-aminophenylacetamido)-2-iodomethyl-4-oxo-1-azetidinyl]thioacetoxyacetic acid

[cis-3-(α-amino-4-hydroxyphenylacetamido)-2-iodomethyl-4-oxo-1-azetidinyl]thioacetoxyacetic acid

[cis-3-(α-amino-4-hydroxy-3-fluorophenylacetamido)-2-iodomethyl-4-oxo-1-azetidinyl]thioacetoxyacetic acid

[cis-3-trifluoromethylmercaptoacetamido-2-iodomethyl-4-oxo-1-azetidinyl]thioacetoxyacetic acid

[cis-3-methylmercaptoacetamido-2-iodomethyl-4-oxo-1-azetidinyl]thioacetoxyacetic acid

[cis-3-methylsulfonylacetamido-2-iodomethyl-4-oxo-1-azetidinyl]thioacetoxyacetic acid

[cis-3-(2′,2′,2′-trifluoroethylsulfinylacetamido)-2-iodomethyl-4-oxo-1-azetidinyl]thioacetoxyacetic acid

[cis-b 3-cyanoacetamido-2-iodomethyl-4-oxo-1-azetidinyl]thioacetoxyacetic acid

[cis-3-cyanomethylmercaptoacetamido-2-iodomethyl-4-oxo-1-azetidinyl]thioacetoxyacetic acid

[cis-3-(α-carboxy-3′-thienylacetamido)-2-iodomethyl-4-oxo-1-azetidinyl]thioacetoxyacetic acid

[cis-3-(α-carboxyphenylacetamido)-2-iodomethyl-4-oxo-1-azetidinyl]thioacetoxyacetic acid

[cis-3-(3′-sydnoneacetamido)-2-iodomethyl-4-oxo-1-azetidinyl]thioacetoxyacetic acid

[cis-3-(1′-tetrazolylacetamido)-2-iodomethyl-4-oxo-1-azetidinyl]thioacetoxyacetic acid

[cis-3-(4′-pyridylmercaptoacetamido)-2-iodomethyl-4-oxo-azetidinyl]thioacetoxyacetic acid

[cis-3-(syn-α-methoxyimino-2′-furylacetamido)-2-iodomethyl-4-oxo-1-azetidinyl]thioacetoxyacetic acid

[cis-3-(2′-aminomethylphenylacetamido)-2-iodomethyl-4-oxo-1-azetidinyl]thioacetoxyacetic acid

[cis-3-(α-oximinophenylacetamido)-2-iodomethyl-4-oxo-1-azetidinyl]thioacetoxyacetic acid

EXAMPLE 18 cis-3-Amino-4-oxo-2-azetidinylmethyl tosylate

A solution of cis-3-azido-4-oxo-2-azetidinylmethyl tosylate (5.0 g) in 50% aqueous acetic acid (50 ml) is cooled and then treated with zinc dust (2.0 g). The reaction is stirred for 30 minutes, filtered, and the solid washed with water (50 ml). The filtrate is saturated with H₂S over ½ hour, the zinc sulfide is removed by filtration and the filtrate evaporated to near dryness. The residue is dissolved in ethyl acetate-water and adjusted to pH 10. Phases are separated and the aqueous layer is extracted with ethyl acetate. The dried organic phases are evaporated to give the amino compound; 3.0 g (66%).

EXAMPLE 19

2-Thienylacetic acid, the 3-amino tosylate from Example 18, and dicyclohexylcarbodiimide (3.7 mmol of each) are stirred in methylene chloride for one hour at 0°. The mixture is diluted with ethyl acetate (150 ml) and filtered; the filtrate is washed with 5% NaHCO₃, dilute HCl, and brine, dried, evaporated and crystallized from acetone-ether to give cis-3-(2-thienylacetamido)-4-oxo-2-azetidinylmethyl tosylate; 0.9 g (69%) mp 121°-124°.

The 3-amino tosylate derivative is acylated with O-formylmandelic acid chloride in the presence of triethylamine at 0° in dry methylene chloride to give cis-3-formylmandelamido-4-oxo-2-azetidinylmethyl tosylate, 98% mp 111°-113° (dec).

The 3-aminotosylate derivative is reacted with an equimolar amount of phenoxyacetyl chloride in dry methylene chloride and in the presence of triethylamine to give cis-3-phenoxyacetamido-4-oxo-2-azetidinylmethyl tosylate; mp 136° (dec).

EXAMPLE 20 cis-3-[α-(t-Butyloxycarbonylamino)-α-phenylacetamido]-4-oxo-2-azetidinylmethyl tosylate To a solution of 2.7 g (0.01 mol) of the 3-amino tosylate of Example 18 in 25 ml of dry methylene chloride is added 2.06 g (0.01 mol) of dicyclohexylcarbodiimide in 5 ml of methylene chloride. The solution is stirred and cooled to 0° under argon and 2.47 grams (0.01 moles) of D(−)-N-t-butyloxycarbonylphenylglycine is dissolved in 50 ml dry methylene chloride and added dropwise over a period of 30 minutes. The dicyclohexylurea is filtered off and washed with methylene chloride. The combined filtrates are evaporated and the residue chromatographed on 100 grams of silica gel. The product 2.1 grams (42%), is eluted with 30% ethyl acetate in methylene chloride.

EXAMPLE 21 cis-3-[α-(t-Butyloxycarbonylamino)-α-phenylacetamido]-4-oxo-2-azetidinylmethyl iodide A mixture of 2 g (3.98 mmol) of product from Example 20, 6 g (40 mmol) of sodium iodide and 150 ml of acetone is thoroughly degassed with argon and then heated at 55°-60° for seven hours. The mixture is cooled to room temperature and the acetone is evaporated. The residue is partitioned between ethyl acetate and water. The organic phase is separated and washed with aqueous sodium thiosulfate and saline. The dried solution is evaporated to give 1.48 g (81%) of the title product.

EXAMPLE 22

Benzhydryl [cis-3-(α-t-Butyloxycarbonylamino-α-phenylacetamido)-2-iodomethyl-4-oxo-1-azetidinyl]hydroxyacetate A suspension of 1.02 g (2.21 mmol) of product from Example 21 in 22 ml of dry tetrahydrofuran is stirred under argon with cooling to −78° and 1.24 ml (2.44 mmol) of a 1.97M n-butyllithium in hexane solution is added. The mixture is stirred for 30 minutes at −78° while 0.66 g (2.75 mmol) of benzhydryl glyoxylate in 20 ml of toluene is dried by distilling off 12 ml of the toluene. The remaining solution is added to the reaction mixture. The resulting mixture is stirred at −78° for 1 hour and then is warmed in an ice bath to 0° for 10 minutes. The reaction is quenched by pouring into cold aqueous $NaH_2PO_4$. The mixture is extracted with ethyl acetate and the combined extracts are washed with saline. The dried solution is evaporated and the residue is taken up in carbon tetrachloride and then hexane is added to precipitate the product, 15 g (97%).

EXAMPLE 23

Benzhydryl [cis-3-(α-t-Butyloxycarbonylamino-α-phenylacetamido)-2-iodomethyl-4-oxoazetidinyl]thioacetoxyacetate To a cold solution (−10°) of 1.5 g (2.21 mmol) of product from Example 22 under argon is added 179 μl (2.21 mmol) of pyridine followed by 157 μl (2.21 mmol) of thionyl chloride. The mixture is stirred for 15 minutes at −10° and then a solution of 252 mg (2.21 mmol) of potassium thiolacetate in 10 ml of dimethylformamide is added. After 15 minutes the solvents are removed in vacuo and the residue is taken up in ethyl acetate and washed with water and saline. The dried solution is evaporated and the residue is chromatographed on silica gel with 20% ethyl acetate in methylene chloride as eluant to give 0.43 g (25.5%) of product.

EXAMPLE 24

(cis-3-α-Aminophenylacetamido-2-iodomethyl-4-oxo-1-azetidinyl)thioacetoxyacetic acid To a cold solution (0°) of 397 mg (0.524 mmol) of ester from Example 23 in 10 ml of methylene chloride is added 1 ml anisole and 9 ml trifluoroacetic acid. The mixture is stirred for 30 minutes at 0°. The solvents are removed in vacuo and the residue is washed with ether and then with hexane. The residual solvent is pumped off to give 230 mg (72%) of title product as its trifluoroacetate salt.

EXAMPLE 25

Treating the acylamino tosylate products prepared in Example 19 with NaI in acetone as set forth in Example 21 gives the following products:

cis-3-(2'-thienylacetamido)-4-oxo-2-azetidinylmethyl iodide, 98% yield cis-3-formylmandelamido-4-oxo-2-azetidinylmethyl iodide cis-3-phenoxyacetamido-4-oxo-2-azetidinylmethyl iodide.

The acylamino tosylate compounds prepared in Examples 19 and 20 are treated with LiBr as in Example 7 to give the following products:

cis-3-(2'-thienylacetamido)-4-oxo-2-azetidinylmethyl bromide cis-3-formylmandelamido-4-oxo-2-azetidinylmethyl bromide cis-3-phenoxyacetamido-4-oxo-2-azetidinylmethyl bromide.

When LiCl and the acylamino tosylate compounds are reacted by the procedure in Example 14 the following products are obtained.

cis-3-(2'-thienylacetamido)-4-oxo-2-azetidinylmethyl chloride cis-3-formylmandelamido-4-oxo-2-azetidinylmethyl chloride cis-3-phenoxyacetamido-4-oxo-2-azetidinylmethyl chloride

EXAMPLE 26

Benzyl [cis-3-(2'-Thienylacetamido)-2-iodomethyl-4-oxo-1-azetidinyl]hydroxyacetate To a suspension of 1.78 g (5.08 mmol) of cis-3-(2'-thienylacetamido)-4-oxo-2-azetidinylmethyl iodide and 2.66 g (16.2 mmol) of freshly distilled benzyl glyoxylate in 44 ml of anhydrous tetrahydrofuran under an argon atmosphere is added 1.31 ml (10.6 mmol) of freshly distilled boron trifluoride etherate. The reaction mixture is stirred at ambient temperature for 1.25 hours, poured into aqueous NaHCO$_3$ and extracted with ethyl acetate. The combined extracts are washed copiously with water and brine. The dried extracts are distilled in vacuo to give 4.5 g of clear orange gum which was rapidly chromatographed on a column of 90 g of silica gel with methylene chloride and 20% ethyl acetate in methylene chloride as eluants to give the title product, 1.66 g (64%).

EXAMPLE 27

Benzyl [cis-3-(2'-Thienylacetamido)-2-iodomethyl-4-oxo-1-azetidinyl]thioacetoxyacetate The product of Example 26 is reacted with pyridine and thionyl chloride at −20° for 45 minutes and then with potassium thiolacetate, all according to the procedure given in Example 9, to give the title product. Recrystallization from ethyl acetate:hexane gave the product as a white crystalline solid, mp 159°–62°.

EXAMPLE 28

[cis-3-(2'-Thienylacetamido)-2-iodomethyl-4-oxoazetidinyl]thioacetoxyacetic acid A solution of 1.05 g (7.6 mmol) of anhydrous potassium carbonate in 50 ml of water is deoxygenated and cooled to 0° under argon. To this mixture is added a solution of 0.796 g (1.39 mmol) of benzyl ester from Example 27 in 36 ml of tetrahydrofuran. The reaction is deoxygenated again and stirred at 0° for ca. 5 min and then without cooling for a total of 1 hour. The mixture is poured into 200 ml of ethyl acetate and extracted with 5% aq. NaHCO$_3$, water and brine. The aqueous extracts are combined, acidified to pH 2 with conc. H$_3$PO$_4$, and then saturated with NaCl. The aqueous solution is extracted with ethyl acetate. The dried extracts are evaporated to give 0.493 g (73%) of crude acid which is chromatographed on silica gel with an eluant of 70:23:5:2 ethyl acetate:acetone:methanol:water. The acid is converted to its sodium salt by treating 0.525 g of the acid with 80 mg NaHCO$_3$ in water and then lyophilizing the solution to obtain the sodium salt.

EXAMPLE 29

Methyl (cis-3-Phenoxyacetamido-2-iodomethyl-4-oxo-1-azetidinyl)hydroxyacetate

A solution of 0.360 g (1.0 mmol) of cis-3-phenoxyacetamido-4-oxo-2-azetidinylmethyl iodide, 0.440 g (5.0 mmol) of methyl glyoxylate, and 246 μl (2.0 mmol) of boron trifluoride etherate in 10 ml of anhydrous tetrahydrofuran is stirred at ambient temperature under an argon atmosphere for 5 hours. At this time 123 μl (1.0 mmol) of boron trifluoride etherate is added and the mixture is stirred for an additional 2 hours. The tetrahydrofuran is removed in vacuo and the residue is taken up in ethyl acetate and extracted with aqueous NaHCO$_3$ and brine. The ethyl acetate solution is dried, filtered and evaporated to give 0.350 g of crude product which is purified by preparative thin-layer chromatography (silica gel GF); 0.174 g of pure product.

EXAMPLE 30

Methyl (cis-3-Phenoxyacetamido-2-iodomethyl-4-oxo-1-azetidinyl) thioacetoxyacetate Methyl (cis-3-phenoxyacetamido-2-iodomethyl-4-oxo-1-azetidinyl)hydroxyacetate (0.174 g, 0.39 mmol) is reacted with 31.5 μl (0.39 mmol) of anhydrous pyridine, followed by 27.8 μl (0.39 mmol) of thionyl chloride as in Example 9. After 30 minutes the solvents are removed in vacuo and a solution of 44.5 mg (0.39 mmol) of potassium thiolacetate in 4 ml of dimethylformamide is added at −10°. After 30 minutes the dimethylformamide is removed in vacuo leaving 0.240 g of crude material which was purified by column chromatography on silica gel to give 0.092 g of the desired thioacetate.

EXAMPLE 31

(cis-3-Phenoxyacetamido-2-iodomethyl-4-oxo-1-azetidinyl)thioacetoxyacetic acid

To a solution of 90 mg of methyl ester from Example 30 in 10 ml of 50% aqueous tetrahydrofuran at 0° is added 1.0 ml of a solution prepared by dissolving 3.3 g of potassium carbonate and 2.0 g of sodium bicarbonate in 40 ml of water (pH 9.2). This mixture is stirred at 0° for 30 minutes and at 25° for one hour and then the tetrahydrofuran is removed in vacuo. Solid sodium chloride is added to the aqueous residue. The solution is adjusted to pH 2 with H$_3$PO$_4$ and extracted with ethyl acetate. The extracts are combined dried and evaporated to give 0.066 g of the desired product.

EXAMPLE 32 cis-3-Azido-4-oxo-2-azetidinylmethyl bromide

A mixture of 0.413 g (1.40 mmol) of cis-3-azido-4-oxo-2-azetidinylmethyl tosylate, 0.434 g (5.0 mmol) of anhydrous lithium bromide and 5 ml of anhydrous dimethylformamide is heated to 100° under argon for one hour. The solution is allowed to cool to 25°, poured into ethyl acetate and extracted copiously with water. The ethyl acetate layer is dried and evaporated to give 0.270 g (94%) of the title product.

EXAMPLE 33

Benzhydryl (cis-3-Azido-4-oxo-2-bromomethyl-1-azetidinyl)hydroxyacetate

A solution of 4.17 g (174 mmol) benzhydryl glyoxylate in 80 ml toluene is heated to reflux under an argon atmosphere and 12 ml of toluene-water mixture is removed by distillation. The remaining solution is cooled to ca. 50° and 2.02 g (9.85 mmol) of cis-3-azido-4-oxo-2-azetidinemethyl bromide is added. The mixture is heated at 90° for 5 hr and then allowed to cool to 25°. The toluene is removed in vacuo to afford 6.05 g of orange gum which is chromatographed on 182 g of silica gel and with 20% ethyl acetate in cyclohexane to give 3.22 g (73%) of product as a mixture of diastereoisomers; tlc: 20% ethyl acetate in cyclohexane; silica gel GF; Rf = 0.37 and 0.29. The lower Rf diastereoisomer was obtained as a crystalline solid, mp 114°–116° (ether).

EXAMPLE 34

Benzhydryl
(cis-3-Azido-4-oxo-2-bromomethyl-1-azetidinly)thioacetoxyacetate

To a sold solution (−20°) of 0.840 g (1.89 mmol) of product from Example 33 in 22 ml of anhydrous tetrahydrofuran under argon is added 193 μl (2.39 mmol) of anhydrous pyridine followed by 172 μl (2.39 mmol) of thionyl chloride. The reaction mixture is stirred at −20° for one hour and then a solution of 0.315 g (2.76 mmol) of potassium thiolacetate in 22 ml of anhydrous dimethylformamide is added. The reaction is stirred at −20° for 30 minutes and then allowed to stand at −23° overnight. The solution is poured into ethyl acetate and extracted copiously with water and then once with 0.1 N boric acid, NaHCO₃ solution and brine. The ethyl acetate layer is dried and evaporated to give 1.0 g of clear, light-yellow gum. This gum is crystallized from ether-hexane first at 25° and then at −23° overnight to give 0.807 g (85%) of the title thioacetate, mp 114°–115.5°. Nuclear magnetic resonance analysis indicated that this material was 2.6:1 mixture of diastereoisomers.

EXAMPLE 35

Benzhydryl
[cis-3-(2′-Thienylacetamido)-2-bromomethyl-4-oxo-1-azetidinyl]thioacetoxyacetate A solution of 0.044 g (0.088 mmol) of benzhydryl ester from Example 34, 0.084 g of platinum oxide, 0.018 g of p-toluenesulfonic acid monohydrate, 3.5 ml of ethyl acetate, and 3.5 ml of ethanol is hydrogenated at ambient temperature and atmospheric pressure for one hour. The mixture is filtered and the solvents are removed in vacuo. The residue is dissolved in 6 ml of anhydrous methylene chloride and cooled to 0° under argon. To this solution is added 24.5 μl of triethylamine followed by 11 μl of thienylacetyl chloride. The reaction mixture is stirred at 0° for one hour and allowed to stand at −23° overnight. The product is isolated by ethyl acetate extraction to afford 0.058 g title product.

Treatment of the above product with trifluoroacetic acid by the procedure of Example 24 gives the same product as in Example 12.

EXAMPLE 36

Benzyl
[cis-3-(2′-Thienylacetamido)-2-(p-tosyloxymethyl)-4-oxo-1-azetidinyl]hydroxyacetate When 1.6 g (4.06 mmol) of cis-3-(2′-thienylacetamido)-4-oxo-2-azetidinylmethyl tosylate, 1.3 g (7.93 mmol) of benzyl glyoxylate (freshly distilled), and 0.85 ml (6.9 mmol) boron trifluoride etherate are reacted together for 3 hours in 75 ml tetrahydrofuran (freshly distilled) according to the procedure of Example 29, the title product is obtained. The product is chromatographed on silica gel with 3:1 chloroform::ethyl acetate as eluant.

EXAMPLE 37

[cis-3-(2′-Thienylacetamido)-2-(p-tosyloxymethyl)-4-oxo-1-azetidinyl]thioacetoxyacetic acid When 1.23 g (2.2 mmol) of the product from Example 36, 0.18 ml (2.23 mmol) pyridine, 0.16 ml (2.22 mmol) thionyl chloride, and 454 mg (3.98 mmol) potassium thiolacetate are reacted according to the procedure of Example 9 benzyl [cis-3-(2′-thienylacetamido)-2-(p-tosyloxymethyl)-4-oxo-1-azetidinyl]thioacetoxyacetate is obtained; 1.56 crude yield, 0.52 g after chromatography on silica gel with 10% ethyl acetate in chloroform as eluant.

The benzyl ester (0.52 g) in 20 ml tetrahydrofuran and 14 ml water is hydrolyzed by the procedure of Example 31 using 6 ml of the base solution to give the title product; 0.11 g. The product is chromatographed on silica gel (1:1 ethyl acetate:chloroform with 0.5% formic acid). The product is dissolved in dioxane, treated with an equivalent of aqueous NaHCO₃ and lyopholized to give the sodium salt.

EXAMPLE 38

[cis-3-(2′-Thienylacetamido)-2-chloromethyl-4-oxo-1-azetidinyl]thioacetoxyacetic acid cis-3-(2′-Thienylacetamido)-4-oxo-2-azetidinylmethyl chloride (1.35 g) is condensed with benzhydryl glyoxalate according to the procedure of Example 22 to give 1.75 g (75%) of the condensation product after chromatography on silica gel with 20% ethyl acetate in chloroform as eluant.

The above product (1.60 g) is converted to benzhydryl [cis-3-(2′-thienylacetamido-2-chloromethyl-4-oxo-1-azetidinyl]thioacetoxyacetate according to the procedure of Example 9; 1.31 g (69%).

The benzhydryl ester (1.24 g) is cleaved according to the procedure of Example 24. The crude product is chromatographed on silica gel (1:1 ethyl acetate:chloroform with 1% formic acid) to give 0.78 g (89%) of title product, which is converted to its sodium salt by the procedure in Example 37.

EXAMPLE 39

[cis-3-(2′-Thienylacetamido)-2-iodomethyl-4-oxo-1-azetidinyl]thiobenzoyloxyacetic acid Benzhydryl cis-3-(2-thienylacetamido)-2-iodomethyl-4-oxo-1-azetidinyl)hydroxyacetate (92 mg) is treated in 5 ml methylene chloride with 11.3 μl thionyl chloride and 12.5 μl pyridine as in Example 9 and then with one-half of a solution of 42.7 mg thiolbenzoic acid and 15 mg NaH in 4 ml dimethylformamide. The product is chromatographed on silica gel with chloroform as eluant; 103 mg.

The benzhydryl ester (100 mg) in 3 ml methylene chloride is treated with 1 ml trifluoroacetic acid for one hour at −10° to 0°. After an acid-base extraction sequence 34 mg of title product is obtained and chromatographed on silica gel with 2% acetic acid in ethyl acetate eluant.

EXAMPLE 40

(cis-3-Mandelamido-2-iodomethyl-4-oxo-1-azetidinyl)-thioacetoxyacetic acid cis-3-(D)-O-Formylmandelamido-4-oxo-2-azetidinylmethyl iodide (0.388 g, 1.0 mmol) is condensed with benzhydryl glyoxylate by the procedure of Example 22. The condensation product is isolated as in Example 22 and then reacted at −20° with 72 μl (1.0 mmol) thionyl chloride and 81 μl (1.0 mmol) pyridine for 30 minutes as in Example 23. The solvents are distilled off at 1 mm pressure and the residue is dissolved in 25 ml dry dimethylformamide and cooled to −25°. A solution of 0.121 g (1.06 mmol) of potassium thiolacetate in 2 ml dimethylformamide is added and the reaction is allowed to stand at −23° for 48 hours. The product is isolated as in Example 23 and chromatographed on silica gel using ethyl acetatebenzene as eluant to give 0.183 g of benzhydryl (cis-3-mandelamido-2-iodomethyl-4-oxo-azetidinyl)thioacetoxyacetate, $[\alpha]_D^{25}$ −18.1° (c 1, CH$_3$OH), and 0.216 g of benzhydryl (cis-3-O-formyl-mandelamido-2-iodomethyl-4-oxo-1-azetidinyl)thioacetoxyacetate.

The benzylhydryl desformyl product is dissolved in dry methylene chloride and stirred with trifluoroacetic acid and anisole at 0° for 20 minutes. The solvents are removed in vacuo and the residue is triturated with hexane and then ether. The product is dissolved in ethyl acetate and precipitated by adding hexane; $[\alpha]_D^{25}$ −24.0 (c 1, CH$_3$OH).

EXAMPLE 41

The alkali metal salts of the compounds of this invention are prepared by treating the compounds with an aqueous solution containing an equivalent of NaHCO$_3$ and lypholizing the solution to obtain salt.

An alternative procedure involves treating a methanol solution of the acid compound with an equivalent of a solution of sodium 2-ethylhexanoate in isopropanol. Ether is added to precipitate the salt.

EXAMPLE 42

An injectable pharmaceutical composition is prepared by dissolving 200 mg of sodium [cis-3-(2'-thienylacetamido)-2-bromomethyl-4-oxo-1-azetidinyl]-thioacetoxyacetate in sterile water or sterile normal saline. Pharmaceutical compositions of other compounds which have antibaterial activity within this invention are prepared as above.

We claim:
1. A compound of the formula

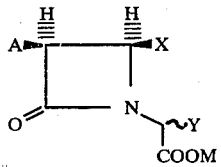

wherein
A is acylamino, amino or protected amino other than acylamino as defined herein;
acyl is

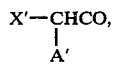

Y'—CH$_2$CO, or Z—S(O)$_n$CH$_2$CO;
X' is thienyl, furyl, cyclohexyl, cyclohexenyl, cyclohexadienyl, phenyl or phenyl substituted with one or two substituents selected from the group consisting of lower alkyl, lower alkoxy, hydroxy, hydroxymethyl, halo, nitro, amino, aminomethyl, mercapto, lower alkylthio, trifluoromethyl, ureido, formamido, and carboxymethylamino;
A' is amino, hydroxy, formyloxy, carboxy, sulfo or (when the α-hydrogen is absent) methoxyimino or oximino;
Y' is cyano, azido, phenyl, phenoxy, 2-aminomethylphenyl, or a heterocyclic ring selected from the group consisting of thienyl, furyl, thiazolyl, isothiazolyl, oxadiazoyl, thiadiazolyl, triazolyl, tetrazolyl, sydnone, pyridyl, and pyrimindyl; each heterocyclic ring being unsubstituted or substituted with one or two substituents selected from lower alkyl, halo, hydroxy, nitro, amino, lower alkoxy or phenyl;
Z is phenyl, pyridyl, lower alkyl, trifluoromethyl, trifluoroethyl or cyanomethyl;
n is 0, 1 or 2;
X is CH$_2$-halogen,

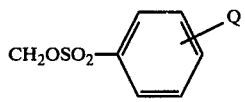

or CH$_2$OSO$_2$R;
R is lower alkyl;
Q is hydrogen, lower alkyl, or halo;
Y is

or hydroxy
E is hydrogen, lower alkyl, trifluoromethyl or phenyl unsubstituted or substituted with one or two substituents selected from the group consisting of lower alkoxy, lower alkyl, halo and nitro; and
M is hydrogen, a carboxylic acid protective ester group or a pharmaceutically acceptable cation.

2. A compound as claimed in claim 1 where A is acylamino; R is methyl or ethyl; Q is hydrogen, methyl or bromo; Y is SCOE; E is methyl or phenyl; and M is hydrogen or a pharmaceutically acceptable cation.

3. A compound as claimed in claim 2 where acyl is mandeloyl, α-formyloxyphenylacetyl, α-aminophenylacetyl, α-amino-4-hydroxyphenylacetyl, α-amino-4-hydroxy-3-fluorophenylacetyl, trifluoromethylmercaptoacetyl, methylmercaptoacetyl, methylsulfonylacetyl, 2,2,2-trifluoroethylsulfinylacetyl, cyanoacetyl, cyanomethylmercaptoacetyl, α-carboxy-2-thienylacetyl, α-carboxy-3-thienylacetyl, α-carboxyphenylacetyl, α-sulfophenylacetyl, 3-sydnoneacetyl, 2-thienylacetyl, 1-tetrazolylacetyl, phenoxyacetyl, phenylacetyl, 4-pyridylmercaptoacetyl, α-synmethoxyimino(2-furyl)acetyl, 2-aminomethylphenylacetyl or α-oximinophenylacetyl.

4. A compound as claimed in claim 3 being the compound (cis-3-phenoxyacetamido-2-iodomethyl-4-oxo-1-azetidinyl)thioacetoxyacetic acid.

5. A compound as claimed in claim 3 being the compound [cis-3-(2'-thienylacetamido)-2-iodomethyl-4-oxo-1-azetidinyl]thioacetoxyacetic acid.

6. A compound as claimed in claim 3 being the compound [cis-3-(2'-thienylacetamido)-2-bromomethyl-4-oxo-1-azetidinyl]thioacetoxyacetic acid.

7. A compound as claimed in claim 3 being the compound [cis-3-(2'-thienylacetamido)-2-chloromethyl-4-oxo-1-azetidinyl]thioacetoxyacetic acid.

8. A compound as claimed in claim 3 being the compound [cis-3-(2'-thienylacetamido)-2-(p-tosyloxymethyl)-4-oxo-1-azetidinyl]thioacetoxyacetic acid.

9. A compound as claimed in claim 3 being the compound [cis-3-(2'-thienylacetamido)-2-iodomethyl-4-oxo-1-azetidinyl]thiobenzoyloxyacetic acid.

10. A compound as claimed in claim 3 being the compound (cis-3-mandelamido-2-iodomethyl-4-oxo-1-azetidinyl)thioacetoxyacetic acid.

11. A compound as claimed in claim 3 being the compound [cis-3-(α-aminophenylacetamido)-2-iodomethyl-4-oxo-1-azetidinyl]thioacetoxyacetic acid.

12. [cis-3-(2,6-dimethoxybenzamido)-2-bromomethyl-4-oxo-1-azetidinyl]thioacetoxyacetic acid.

13. A compound as claimed in claim 1 where A is protected amino; R is methyl or ethyl; Q is hydrogen, methyl, or bromo; E is methyl or phenyl; and M is hydrogen or a carboxylic acid protecting ester group.

14. A compound as claimed in claim 13 where the protected amino group is t-butoxycarbonylamino, trichloroethoxycarbonylamino, benzyloxycarbonylamino, p-methoxybenzyloxycarbonylamino, p-nitrobenzoyloxycarbonylamino, isobornyloxycarbonylamino, phthalimido, succinimido, maleimido or 4,5-diphenyl-4-oxoazolin-2-one and M is hydrogen, 2,2,2-trichloroethyl, benzyl, benzhydryl, t-butyl or methyl.

15. A compound as claimed in claim 14 being the compound (cis-3-isobornyloxycarbonylamino-2-iodomethyl-4-oxo-1-azetidinyl)thioacetoxyacetic acid or the benzyl, benzylhydryl, t-butyl, or methyl ester thereof.

16. A compound as claimed in claim 14 being the compound (cis-3-isobornyloxycarbonylamino-2-bromomethyl-4-oxo-1-azetidinyl)thioacetoxyacetic acid or the benzyl, benzhydryl, t-butyl, or methyl ester thereof.

17. A compound as claimed in claim 14 being the compound (cis-3-isobornyloxycarbonylamino-2-chloromethyl-4-oxo-1-azetidinyl)thioacetoxyacetic acid or the benzyl, benzhydryl, t-butyl, or methyl ester thereof.

18. A compound as claimed in claim 14 being the compound (cis-3-isobornyloxycarbonylamino-2-(p-tosyloxymethyl)-4-oxo-1-azetidinyl)thioacetoxyacetic acid or the benzyl, benzhydryl, t-butyl, or methyl ester thereof.

19. A compound as claimed in claim 14 being the compound (cis-3-t-butoxycarbonylamino-2-bromomethyl-4-oxo-1-azetidinyl)thioacetoxyacetic acid or the benzyl, benzhydryl, t-butyl, or methyl ester thereof.

20. A compound as claimed in claim 1 where A is amino, Q is hydrogen, methyl, or bromo; E is methyl or phenyl; and M is hydrogen or a carboxylic acid protective ester group.

21. A compound as claimed in claim 20 where M is hydrogen, 2,2,2-trichloroethyl, benzyl, benzhydryl, t-butyl, or methyl.

22. A compound as claimed in claim 21 being the compound (cis-3-amino-2-iodomethyl-4-oxo-1-azetidinyl)thioacetoxyacetic acid.

23. A compound as claimed in claim 21 being the compound (cis-3-amino-2-bromomethyl-4-oxo-1-azetidinyl)thioacetoxyacetic acid.

24. A compound as claimed in claim 21 being the compound (cis-3-amino-2-chloromethyl-4-oxo-1-azetidinyl)thioacetoxyacetic acid.

25. A compound as claimed in claim 21 being the compound (cis-3-amino-2-(p-tosyloxymethyl)-4-oxo-1-azetidinyl)thioacetoxyacetic acid.

26. A pharmaceutical composition comprising a pharmaceutically acceptable carrier and an antibacterially effective amount of a compound as claimed in claim 2.

27. A method of treating bacterial infections in subject in need thereof comprising administering internally to said subject an antibacterially effective non-toxic quantity of a compound as claimed in claim 2.

28. A compound as claimed in claim 1 where Y is hydroxy, A is protected amino or acylamino; R is methyl or ethyl; Q is hydrogen, methyl or bromo and M is a carboxylic acid protective ester group.

* * * * *